(12) United States Patent
Wahlstrom et al.

(10) Patent No.: US 7,463,933 B2
(45) Date of Patent: Dec. 9, 2008

(54) LEAD RETENTION MEANS

(75) Inventors: Dale A. Wahlstrom, Plymouth, MN (US); Jay A. Erlebacher, Tenafly, NJ (US); John L. Sommer, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 10/870,211

(22) Filed: Jun. 17, 2004

(65) Prior Publication Data

US 2005/0171588 A1   Aug. 4, 2005

Related U.S. Application Data

(63) Continuation-in-part of application No. 10/771,643, filed on Feb. 4, 2004, now Pat. No. 7,212,869.

(51) Int. Cl.
*A61N 1/00* (2006.01)
(52) U.S. Cl. .................................................. 607/126
(58) Field of Classification Search ............. 607/116, 607/118, 126, 128, 130–131, 122–123; 600/373–375; 606/72; 604/175
See application file for complete search history.

(56) References Cited

U.S. PATENT DOCUMENTS

| | | | | |
|---|---|---|---|---|
| 3,123,077 A * | 3/1964 | Alcamo | ...................... | 606/228 |
| 3,939,843 A * | 2/1976 | Smyth | ........................ | 607/126 |
| 3,981,051 A * | 9/1976 | Brumlik | ...................... | 24/447 |
| 4,272,577 A | 6/1981 | Lyng | .......................... | 428/112 |
| 4,490,326 A | 12/1984 | Beroff et al. | ........... | 264/328.16 |
| 4,827,940 A | 5/1989 | Mayer et al. | ................ | 128/642 |
| 4,841,971 A | 6/1989 | Hess | ........................ | 128/419 P |
| 4,876,109 A | 10/1989 | Mayer et al. | .................... | 427/2 |
| 5,011,494 A | 4/1991 | von Recum et al. | ........... | 623/11 |
| 5,219,361 A | 6/1993 | von Recum et al. | ........... | 623/11 |
| 5,300,107 A | 4/1994 | Stokes et al. | ................. | 607/126 |
| 5,573,547 A * | 11/1996 | LeVeen et al. | .............. | 606/232 |
| 5,580,699 A | 12/1996 | Layman et al. | ............. | 430/311 |
| 5,733,322 A | 3/1998 | Starkebaum | ................. | 607/117 |
| 5,830,217 A * | 11/1998 | Ryan | .......................... | 623/1.11 |
| 5,911,733 A * | 6/1999 | Parodi | ........................ | 623/1.15 |
| 5,925,073 A | 7/1999 | Chastain et al. | | |
| 5,984,896 A * | 11/1999 | Boyd | .......................... | 604/175 |
| 5,991,668 A * | 11/1999 | Leinders et al. | ............. | 607/125 |
| 5,999,858 A | 12/1999 | Sommer et al. | ............. | 607/122 |
| 6,006,122 A | 12/1999 | Smits | .......................... | 600/373 |
| 6,083,247 A | 7/2000 | Rutten et al. | | |
| 6,144,882 A | 11/2000 | Sommer et al. | ............. | 607/126 |
| 6,147,135 A * | 11/2000 | Yuan et al. | ................... | 523/105 |
| 6,173,206 B1 | 1/2001 | Shchervinsky | .............. | 607/132 |
| 6,178,356 B1 | 1/2001 | Chastain et al. | | |
| 6,240,322 B1 | 5/2001 | Peterfeso et al. | | |
| 6,263,249 B1 | 7/2001 | Stewart et al. | .............. | 607/116 |
| 6,304,786 B1 | 10/2001 | Heil, Jr. et al. | .............. | 607/126 |
| 6,477,423 B1 * | 11/2002 | Jenkins | ........................ | 607/40 |
| 6,549,811 B2 | 4/2003 | Stewart et al. | .............. | 607/116 |
| 6,594,515 B2 * | 7/2003 | Watson | ........................ | 600/376 |
| 6,692,499 B2 * | 2/2004 | Tormala et al. | ................ | 606/72 |
| 6,773,450 B2 * | 8/2004 | Leung et al. | ................. | 606/232 |
| 6,846,296 B1 * | 1/2005 | Milbocker et al. | .......... | 601/153 |

(Continued)

*Primary Examiner*—Mark W Bockelman
(74) *Attorney, Agent, or Firm*—Michael C. Soldner

(57) ABSTRACT

An elongate body of a medical device includes at least one retaining segment extending along a length of the body, the retaining segment including a plurality of fish-like scales directed in a first common direction.

23 Claims, 11 Drawing Sheets

U.S. PATENT DOCUMENTS

2001/0044646 A1* 11/2001 Marshall et al. ............. 607/127
2003/0199961 A1 10/2003 Bjorklund et al.
2003/0199962 A1 10/2003 Struble et al. ............... 607/126
2004/0230282 A1* 11/2004 Cates et al. ................. 607/126

* cited by examiner

US 7,463,933 B2

LEAD RETENTION MEANS

RELATED APPLICATION

This application is a continuation-in-part of application Ser. No. 10/771,643 filed on Feb. 4, 2004 and entitled "Novel Lead Retention Means" which is now U.S. Pat. No. 7,212,869.

TECHNICAL FIELD

The present invention relates to medical devices and more particularly to means for retaining or preventing dislodgement of a lead positioned within a body.

BACKGROUND

Medical devices often include a therapy generator and one or more elongate leads, coupled thereto, which are positioned within a patient's body to deliver therapy from the generator. Such therapy may be in the form of electrical stimulation, delivered via electrical conductors extending through a lead body, or fluid infusion, delivered via a lumen extending through a lead body. Some examples of electrical stimulation include pacing and defibrillation; some examples of fluids, which may be infused, include drugs, nutrients, and genetic materials. In many applications, leads are inserted through one or more blood vessels and are ultimately positioned within a blood vessel where the lead must be retained for a period of time in order to deliver the therapy. Therefore it is desirable to provide lead retention means allowing insertion or forward motion of lead, to position the lead within a vessel, while preventing further forward motion and rearward motion of the lead during subsequent therapy delivery.

BRIEF DESCRIPTION OF THE DRAWINGS

The following drawings are illustrative of particular embodiments of the invention and therefore do not limit its scope, but are presented to assist in providing a proper understanding of the invention. The drawings are not to scale (unless so stated) and are intended for use in conjunction with the explanations in the following detailed description. The present invention will hereinafter be described in conjunction with the appended drawings, wherein like numerals denote like elements, and.

DETAILED DESCRIPTION

The following detailed description is exemplary in nature and is not intended to limit the scope, applicability, or configuration of the invention in any way. Rather, the following description provides a practical illustration for implementing exemplary embodiments of the invention.

Figure 1:
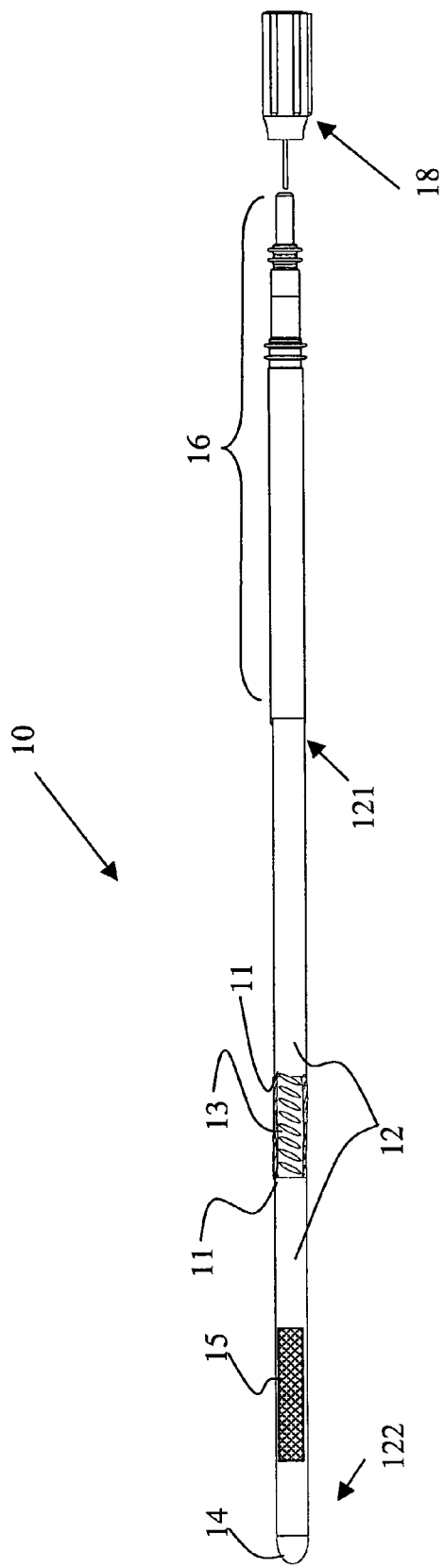
FIG. 1 is a plan view with a partial section of a lead including means for retention according to one embodiment of the present invention.

FIG. 1 is a plan view with a partial section of a lead 10 including means for retention 15 according to one embodiment of the present invention. FIG. 1 illustrates lead 10 including a lead body 12, a connector 16 coupled to a proximal end 121 of the lead body 12 and an electrode 14 coupled to a distal end 122 of the lead body 12; a conductor 13, extending within an outer sheath 11, couples electrode 14 to connector 16, in order to deliver electrical stimulation, and forms a lumen for slideably engaging a stylet 18. Means and materials for constructing such a lead are well known to those skilled in the art.

Figure 6:
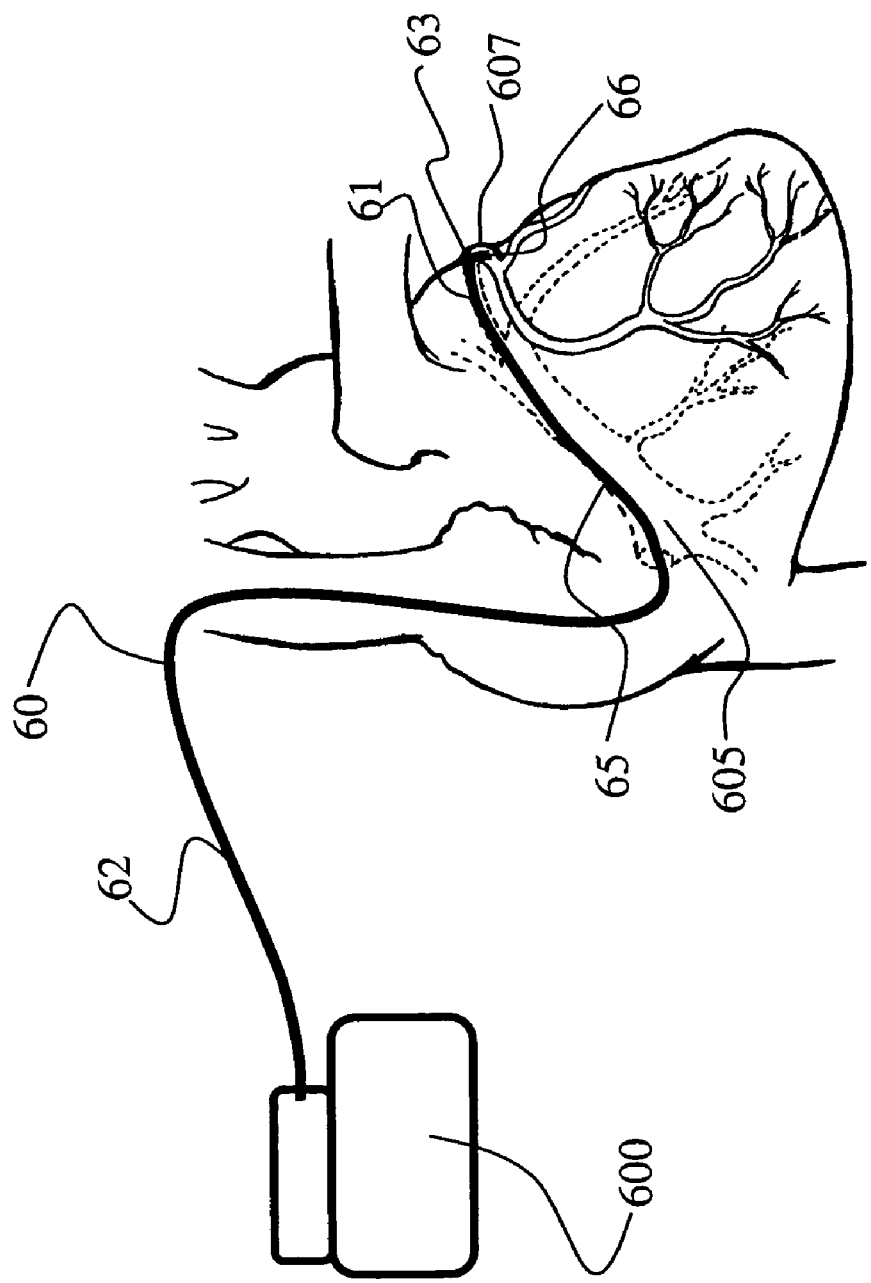
FIG. 6 is a schematic view of a medical device, which may incorporate retention means according to embodiments of the present invention.

FIG. 1 further illustrates retention means 15 formed along an outer surface of lead body 12 in proximity to distal end 122. According to embodiments of the present invention, retention means 15 allows insertion of lead body 12 through a vessel, for example a vessel 607 as illustrated in FIG. 6, while preventing retraction of lead body 12 within the vessel due to an interference of retention means 15 along a wall of the vessel that contacts lead body 12. Retention means according to some embodiments of the present invention extends along a length greater than or equal to approximately 1 mm and may be implemented along any portion of a lead body alone or in conjunction with other retention means; further, retention means 15 may be an integral part of outer sheath 11 or may be formed on a separate collar fitted about lead body 12, either in-line with or about outer sheath 11. Suitable materials for outer sheath 11 and retention means 15 include those that are biocompatible, examples of which include, but are not limited to, silicone and polyurethane.

Figure 2A:
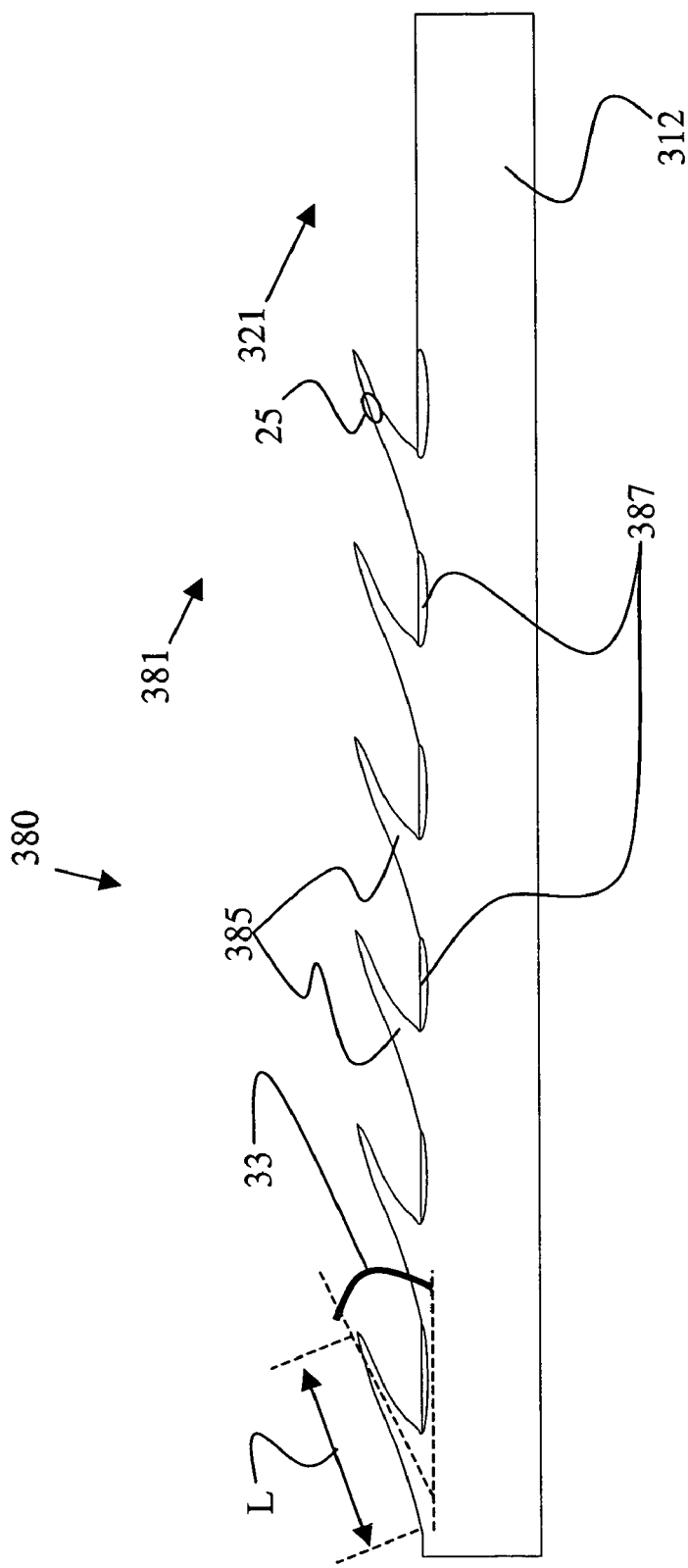
FIG. 2A is an enlarged plan view of a retention means according to one embodiment of the present invention.
Figure 2B:
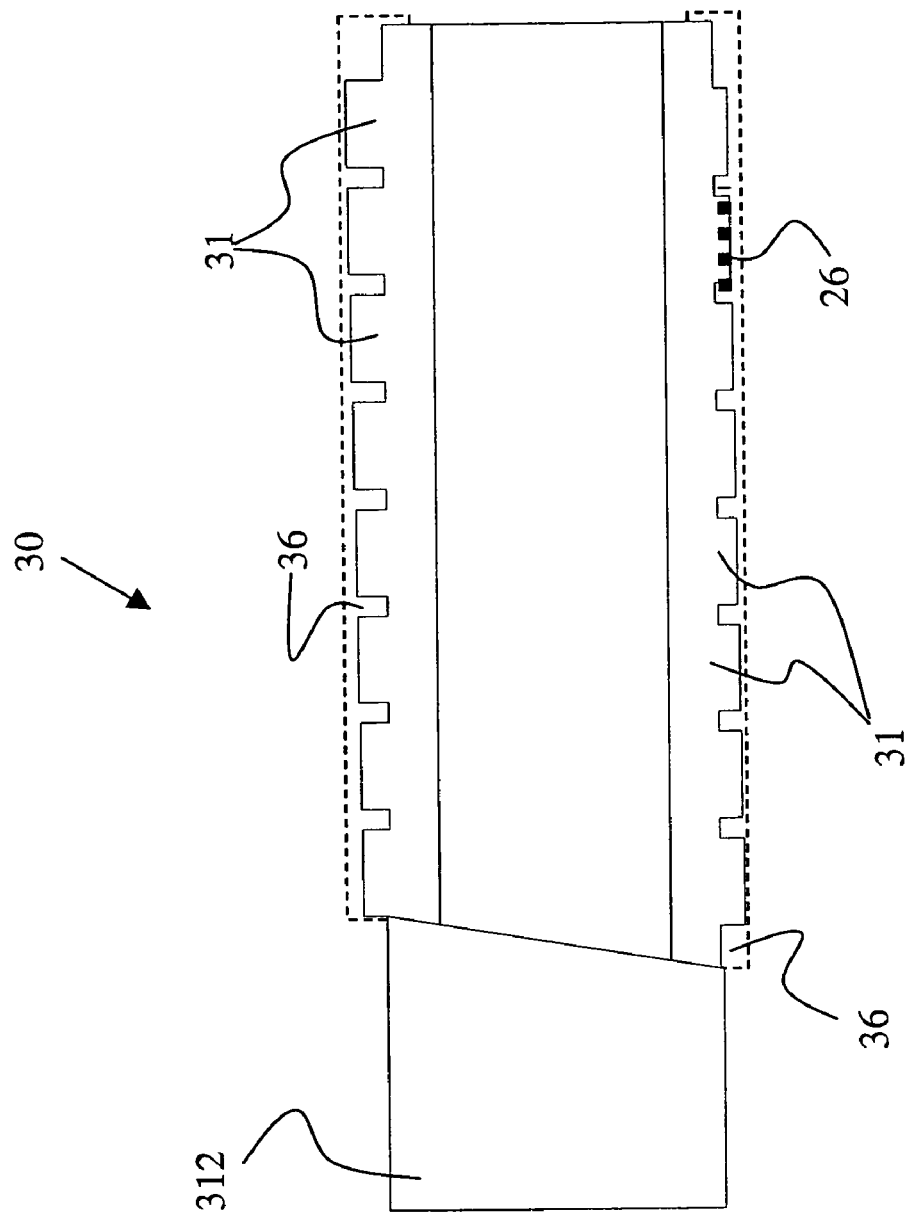
FIG. 2B is an enlarged partial section view of means for retention according to an alternate embodiment.
Figure 2C:
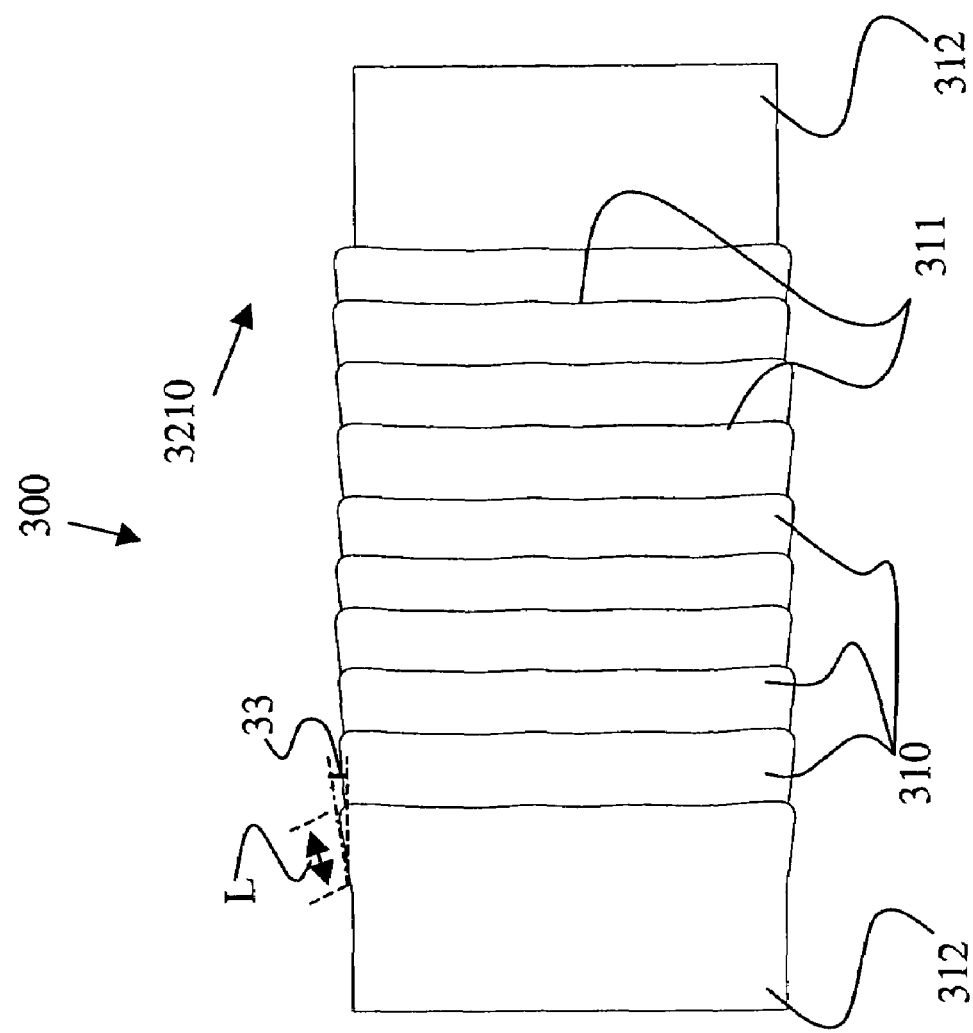
FIG. 2C is an enlarged plan view of means for retention according to another embodiment.
Figure 2D:
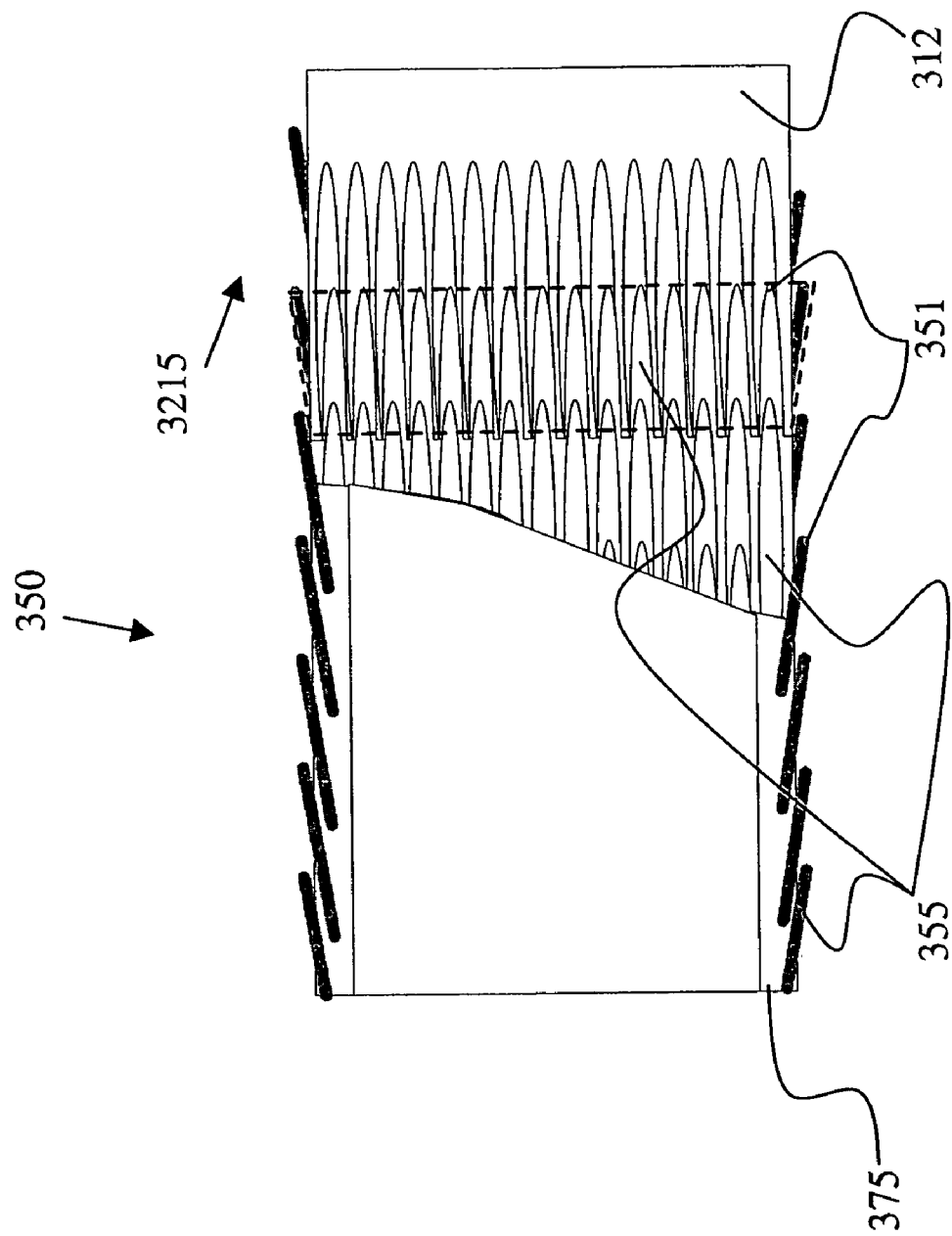
FIG. 2D is an enlarged partial section view of means for retention according to yet another embodiment of the present invention.

Various embodiments of retention means include projections formed along retaining segments as illustrated in FIGS. 2A-D and 4A-5B. It should be noted that alternate embodiments include, but are not limited to, retaining segments extending around an entire circumference of a lead body and segments extending only about a portion of the circumference of the lead body. For example, a plurality of projections may lie in a line, single file, along a length of a retaining segment, as illustrated in FIG. 2A, or each individual projection may extend circumferentially about all or a portion of a retaining segment, as illustrated in FIG. 2C, or a plurality of projections may lie approximately side-by-side about all or a portion of a circumference, as illustrated in FIG. 2D.

In some embodiments, retaining segments as a whole or just the projections may be formed of a bioabsorbable material, examples of which include those taught in lines 10-24 of U.S. Pat. No. 6,173,206. According to these embodiments, if a lead body is chronically implanted, the retaining segment or projections would remain intact long enough to hold the body in place for a period of time up to tissue encapsulation of the body; this may facilitate extraction of a chronically implanted lead. One example of an appropriate bioabsorbable material, polydioxanone is described along with means for molding the material in U.S. Pat. No. 4,490,326, the teachings of which are incorporated by reference herein.

FIG. 2A is an enlarged plan view of means for retention according to one embodiment of the present invention. FIG. 2A illustrates a retaining segment 380 including a plurality of barb-like projections 385 positioned in a single-file line along a length of the segment 380; each of the plurality of projections 385 include a length L and extend laterally from a lead body 312 toward a proximal end 321 at an angle 33, which, according to some embodiments, is less than approximately 45 degrees. According to this embodiment of the present invention and various other embodiments illustrated herein length L is greater than approximately 100 microns. FIG. 2A further illustrates projections 385 as portions of a wall 387 forming retaining segment, having been lifted out of wall 387 according to one embodiment of the present invention. FIG. 2B illustrates an alternate retaining segment 30 extending along a length of lead body 312 and including tread-like projections 31 extending laterally from lead body 312 to form a textured surface adapted to engage a vessel wall, similar to, for example, a sole of a shoe designed to facilitate traction. According to some embodiments of the present invention, projections, i.e. 385, 31, are directly formed in outer surfaces, being integral with a bulk material underlying the surfaces, but, according to alternate embodiments, the projections are formed of separate materials either embedded in or adhered to these surfaces. Alternative methods of forming examples of these embodiments will be described herein below.

FIG. 2B further illustrates retaining segment 30 including a coating 36, which is soluble in body fluids; according to this embodiment, coating 36 fills in around projections 31 and remains intact temporarily, during positioning of lead body 312, so that lead body 312 may be moved back and forth through a vessel if repositioning is necessary. Suitable materials forming coating 36 are soluble in body fluids (within a temperature range encompassing normal body temperature), non-toxic, biocompatible and non-pyrogenic; examples of such a material include sugar derivatives, such as mannitol and dextrose, salts, such as sodium chloride and potassium chloride, and polyvinylpyrrolidone (PVP). Portions of U.S. Pat. No. 4,827,940 teaching methods for forming and applying a mannitol solution are incorporated by reference herein. According to an alternate embodiment, a covering in the form of a thin wall tube may be deployed over retaining segment 30 in place of coating 36. It should be noted that any of the embodiments described herein may include such a coating or a covering facilitating positioning of lead bodies.

FIG. 2C is an enlarged plan view of means for retention according to another embodiment. FIG. 2C illustrates a retaining segment 300 coupled to a portion of lead body 312 and including a proximal end 3210 and a plurality of projections 310, each of which extend around all or a portion of a circumference of lead body 312 and extend laterally from lead body 312 at angle 33 with terminal ends 311 of projections 310 directed toward proximal end 3210.

FIG. 2D is an enlarged partial section view of means for retention according to yet another embodiment of the present invention. FIG. 2D illustrates a retaining segment 350 including a plurality of fish scale-like projections 355 positioned side-by-side about a circumference of lead body 312 and along a length of segment 350, and including terminal ends 351 directed toward a proximal end 3215. Projections 355 of figure 2D are shown positioned in an overlapping pattern, for example, disposed in multiple circumferential rows and each circumferential row of scales is disposed in offset relation to an adjacent circumferential row of scales; FIG. 7B further illustrates a variation in an offset relation of rows of scales according to another embodiment.

FIG. 2D further illustrates projections 355 as discrete elements embedded in an underlying surface 375 of segment 350 according to one embodiment of the present invention. Fish scale-like projections 355 may be arranged in a manner of actual fish scales of which there are four main types, each type having numerous variations; the four main types are: a.) Placoid, b.) Cosmoid, c.) Ganoid and d.) Cycloid and ctenoid. According to various embodiments of the present invention, projections 355 may take on any of forms and be arranged in any of the manners described by these four main types of actual fish scales.

Retaining segment 350 is characterized in allowing movement of body 312 within a vessel in a first direction to an implanted position while preventing movement of body 312 from the implanted position in the opposite direction. Thus, a tendency for lead body 312 to dislodge from the implanted position in the vessel would be prevented by terminal ends 351 of fish scale-like projections 355, which engage a wall of the vessel. Such projections 355 have an advantage over standard tine structures, which are commonly found on implantable leads known in the art, in that the lead fixation achieved by projections 355 is independent of the geometry of the implant site in the vessel. One may conceptualize the fixation afforded by projections 355 as "micro-fixation" as opposed to a "macro-fixation" of conventional tines or a screw. According to some embodiments of the present invention, this "micro-fixation" is further enhanced by a curvature formed in body 312, resulting, for example, in a serpentine shape, which encourages contact of projections 355 with the vessel wall at the implant site. Methods, which may be employed to keep body 312 straight during implantation, include use of a stylet wire within body 312 or a catheter external to body 312 and are well known to those skilled in the art. Furthermore according to some embodiments, a coating, for example coating 36 described in conjunction with FIG. 2B, is formed over retaining segment 350 to protect projections 355 during implantation.

FIG. 2D also illustrates, by way of a dashed line connecting projections 355 around a circumference, another embodiment in which embedded elements forming projections may be rings or portions of a coil circling a portion of or the entire circumference of segment 350 creating projections similar to projections 310 illustrated in FIG. 2C.

According to further alternate embodiments, some or all projections of a retaining segment, for example projections 385, 31, 310 and 355 (FIGS. 2A-D), each include microfeatures further enhancing engagement of the projections with the vessel wall. In FIG. 2A such a feature is illustrated on one of projections 385 as a hole or indentation 25; in FIG. 2B such a feature is illustrated as a modified surface 26 on one of projections 31 wherein surface 26 includes texture, adhesive spots, or some material promoting thrombotic adhesion to vessel wall.

Methods for forming various embodiments of retaining segments, for example those depicted in FIGS. 2A-D, include, but are not limited to, molding, extrusion, cutting, laser ablation, and coating. These methods may form projections directly in outer surfaces, such that they are integral with a bulk material underlying the surfaces, or may integrate the projections with the surface by embedding or adhering.

According to some embodiments of the present invention, transfer or injection molding, using methods known to those skilled in the art, are used to form a retaining segment including projections, examples of which include those depicted in FIGS. 2B-C. According to other embodiments, a cutting process may be used to create projections on a retaining segment, for example segment 380 illustrated in FIG. 2A; a blade may be used to nick the surface or to cut all the way through a wall of the retaining segment.

Alternatively, laser ablation may be used to create projections from a bulk material of a retaining segment, i.e. FIGS. 2B-C, or by exposing, at a surface of the segment, portions of materials which have been embedded within the bulk material underlying the surface during, for example, a molding or extrusion process, i.e. FIG. 2D. U.S. Pat. No. 5,580,699 describes a suitable laser ablation process, which may be used to form retaining segments and the pertinent teachings of the '699 patent are incorporated by reference herein. U.S. Pat. No. 4,272,577 describes an extrusion process for forming ski bases having direction-dependent friction coefficients wherein harder particles, within a plastic matrix flowing through a slit nozzle, become obliquely oriented relative to the surface of the base; in one case, by means of a temperature gradient across the nozzle. We contemplate that similar methods may be developed by those skilled in the art, according to the teachings of the '577 patent, in order to extrude retaining segments according to the present invention, and incorporate by reference the pertinent teachings of the '577 patent herein. Some composite materials suitable for embodiments of the present invention include but are not limited to polyamide and polyimide particles, polyester fibers, carbon fibers or particles and any combination thereof blended with silicone.

According to further alternate embodiments a coating applied to a surface of a retaining segment may form projections and or micro-features on projections, for example similar to those illustrated in FIGS. 2B-C. Stewart et al. describe an example of a suitable coating process via plasma deposition in commonly assigned U.S. Pat. No. 6,549,811, which is incorporated by reference in its entirety herein. Furthermore coatings including particles blended within, for example a silicone medical adhesive including biocompatible metal particles or hard plastic particles may form an embodiment of the present invention for example similar to those illustrated in FIGS. 2B and 2D.

Figure 3:
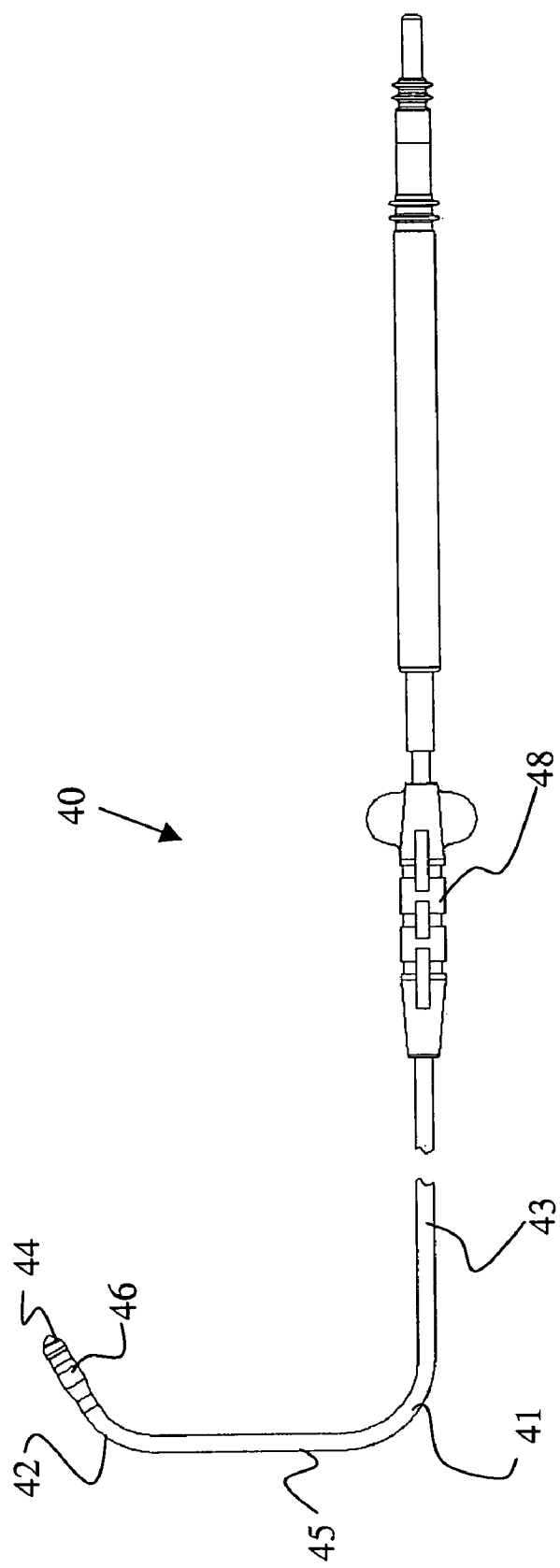
FIG. 3 is a plan view of a lead which may incorporate retention means according to embodiments of the present invention.

FIG. 3 is a plan view of a lead 40, which may incorporate retention means according to embodiments of the present invention. FIG. 3 illustrates lead 40 including a proximal portion 43, a first preformed bend 41 extending from proximal portion 43 to an intermediate segment 45 and a second preformed bend 42 extending from intermediate segment 45 to distal segment 46, which is terminated by a tip 44. Such a lead is fully described in commonly assigned U.S. Pat. No. 5,999,858, which is herein incorporated by reference in its entirety. According to embodiments of the present invention, first and second bends 41 and 42 acting as means for retention of lead body in a coronary vessel, for example a coronary sinus 605 or a branch vessel 607 thereof illustrated in FIG. 6, are supplemented by any of the retaining segments described herein, which may be formed along the lead body surface at first bend 41, intermediate segment 45, second bend 42, distal segment 46, or any combination thereof. Any other combination of bends within a lead body is within the scope of the present invention, for example that resulting in a serpentine shape, as previously described.

Figure 4B:
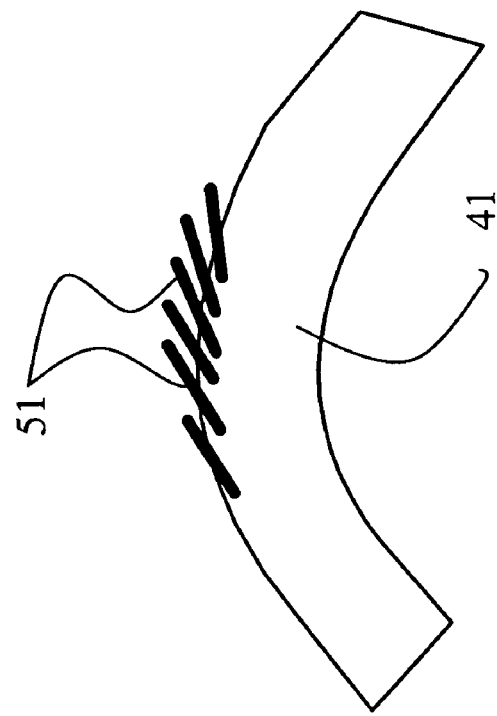
FIGS. 4A-B are plan views of a portion of a lead body including retention means according to an alternate embodiment of the present invention.
Figure 4A:
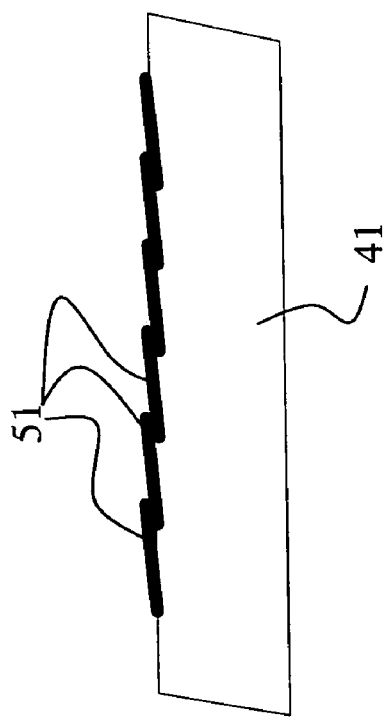

FIGS. 4A-B are partial plan views of one embodiment of lead 40 showing only a portion at first bend 41, which includes a retaining segment formed by projections 51. According to some embodiments of the present invention a retaining segment may be activated by a bending of a lead body as illustrated in FIGS. 4A-B. If a stylet, for example stylet 18 shown in FIG. 1, is inserted into lead 40 to straighten preformed bend 41, projections 51 become approximately parallel with an outer surface of lead 40, as illustrated in FIG. 4A. Once the stylet is removed preformed bend 41 reforms such that projections 51 protrude laterally and are thus activated to prevent rearward motion of lead 40 within a vessel. If it becomes necessary to reposition lead 40, the stylet may be reinserted to straighten bend 41 thus bringing projections into approximate alignment with the surface of lead 40. It should be noted that the embodiment illustrated in FIG. 2D may be of the type illustrated in FIGS. 4A-B.

FIG. 3 further illustrates lead 40 including an anchoring sleeve 48 positioned about proximal portion 43 thereof. According to an additional embodiment of the present invention, means for retention as illustrated herein, may be formed along an outer surface of proximal portion to provide frictional forces complementing anchoring sleeve 48 at a venous entry point. The means for retention may either engage an inner surface of anchoring sleeve 48 or engage a vein wall in proximity to the entry point.

Figure 5A:
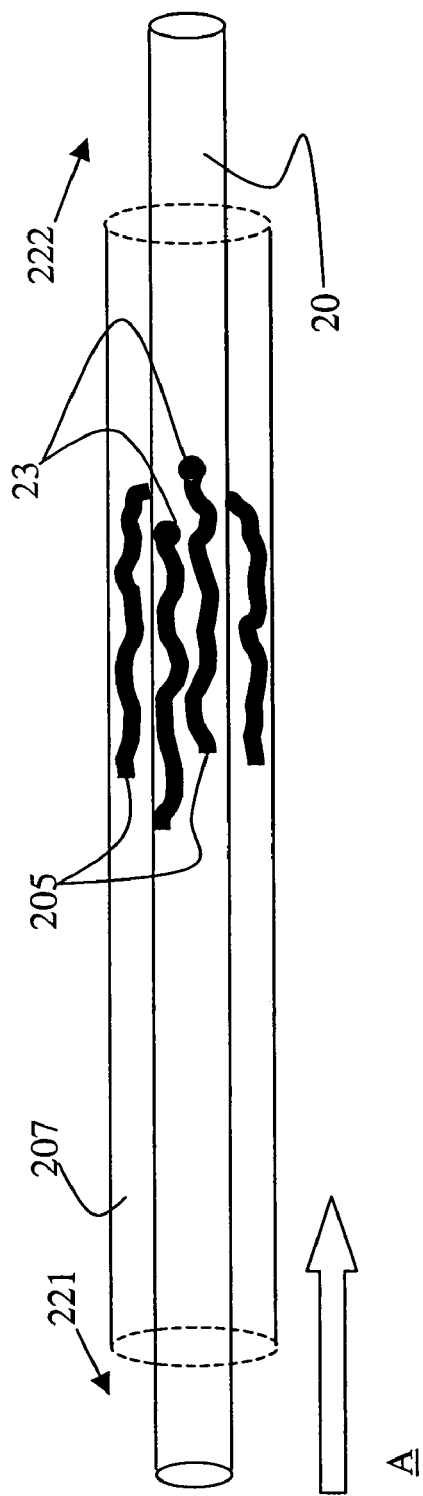
FIGS. 5A-B are schematic views of a portion of a lead body including retention means according to yet another embodiment of the present invention.
Figure 5B:
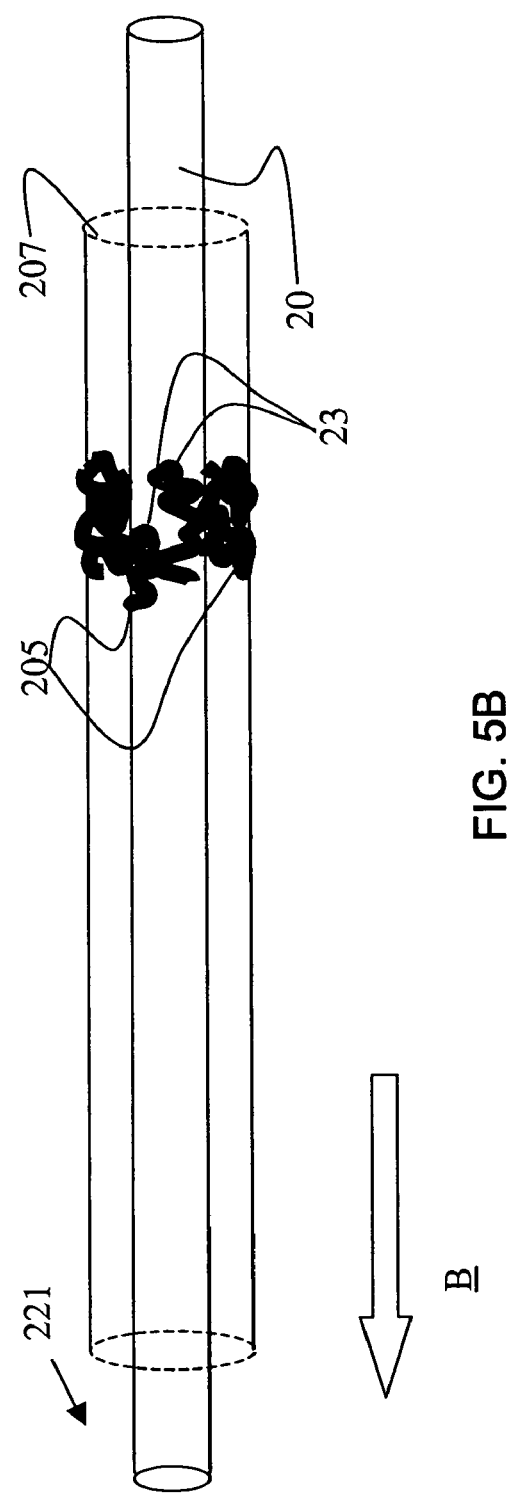

FIGS. 5A-B schematic views of a portion of a lead body including retention means according to yet another embodiment. FIGS. 5A-B illustrate a lead body 20 including a plurality of hair-like projections or fibers 205 each attached at one end to lead body 20 and directed by their attachment points 23 to extend out from and along a length of body 20 toward a proximal end 221 of body 20. According to the illustrated embodiment, as lead body 20 is advanced distally in a vessel 207 per arrow A, as in FIG. 5A, projections 205 are suspended proximally; when lead body 20 is retracted proximally per arrow B, as in FIG. 5B, projections 205 are forced toward a distal end 222 of body 20 to become bunched up and wedged between body 20 and a wall of vessel 207, thereby providing retention means for lead body 20. Projections may be formed from a bioabsorbable polymer, for example polyglycolic acid or polylactic acid. Alternately projections 205 may be formed from polyester fibers or some other material promoting thrombotic adhesion with the vessel wall to enhance retention within vessel 207; such thrombotic projections may include a non-thrombogenic coating adapted to dissolve after the lead is positioned per FIG. 5B, examples of which include a benzalkonium chloride-heparin solution and polyvinylpyrrolidone. Projections 205 may be attached at attachment points 23 by embedment within lead body 20 or by adhesive attachment, for example by means of silicone medical adhesive.

FIG. 6 is a schematic view of an exemplary medical device, which may incorporate retention means according to embodiments of the present invention. FIG. 6 illustrates the medical device including a therapy generator 600 coupled to a lead 60 implanted within branch vessel 607 emanating from coronary sinus 605. Lead 60 including a connector terminating a proximal portion 62, an electrode in proximity to a distal end 66 and a conductor extending through an outer insulative sheath (similar to lead 10 illustrated in FIG. 1) may deliver electrical therapy, or may deliver infusions of therapeutic fluids from generator 600 through a central lumen. FIG. 6 further illustrates potential retention segment sites 65, 61, and 63 along lead 60 where projections of retention segments according to embodiments of the present invention would engage a wall of vessels 605 and 607 to prevent rearward dislodgment of lead 60 from vessel 607.

Figure 7A:
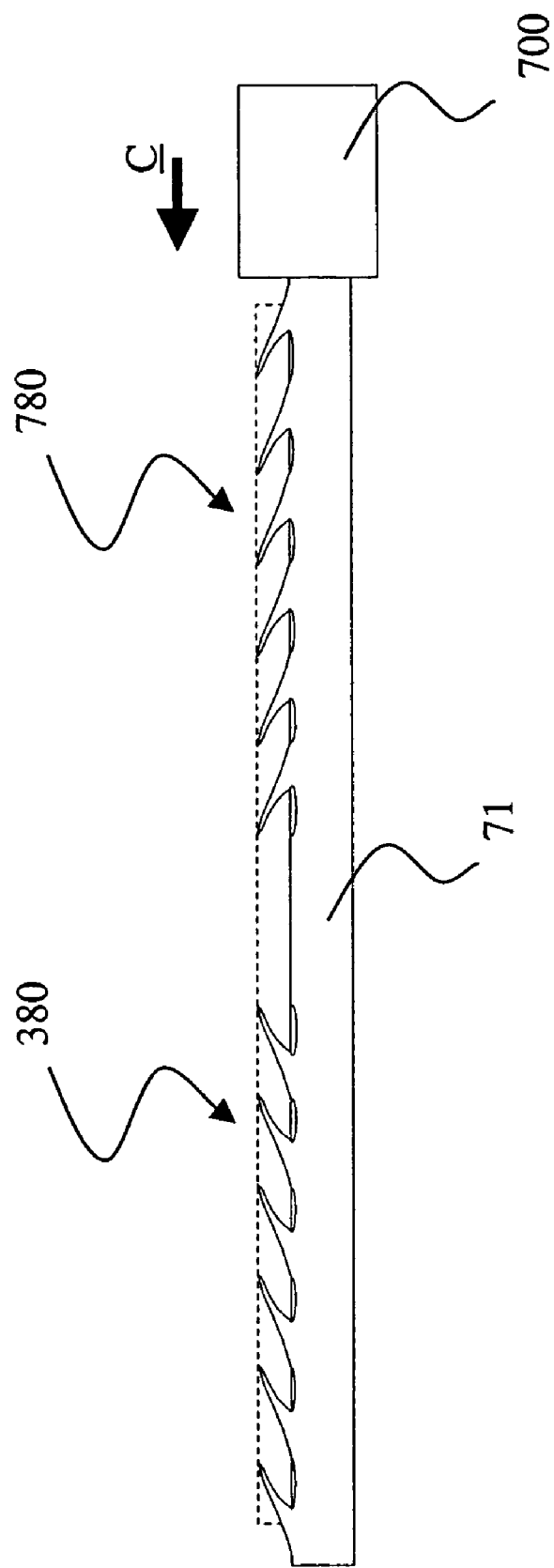
FIG. 7A-B are plan views of lead distal portions including retention means according to additional embodiments of the present invention.
Figure 7B:
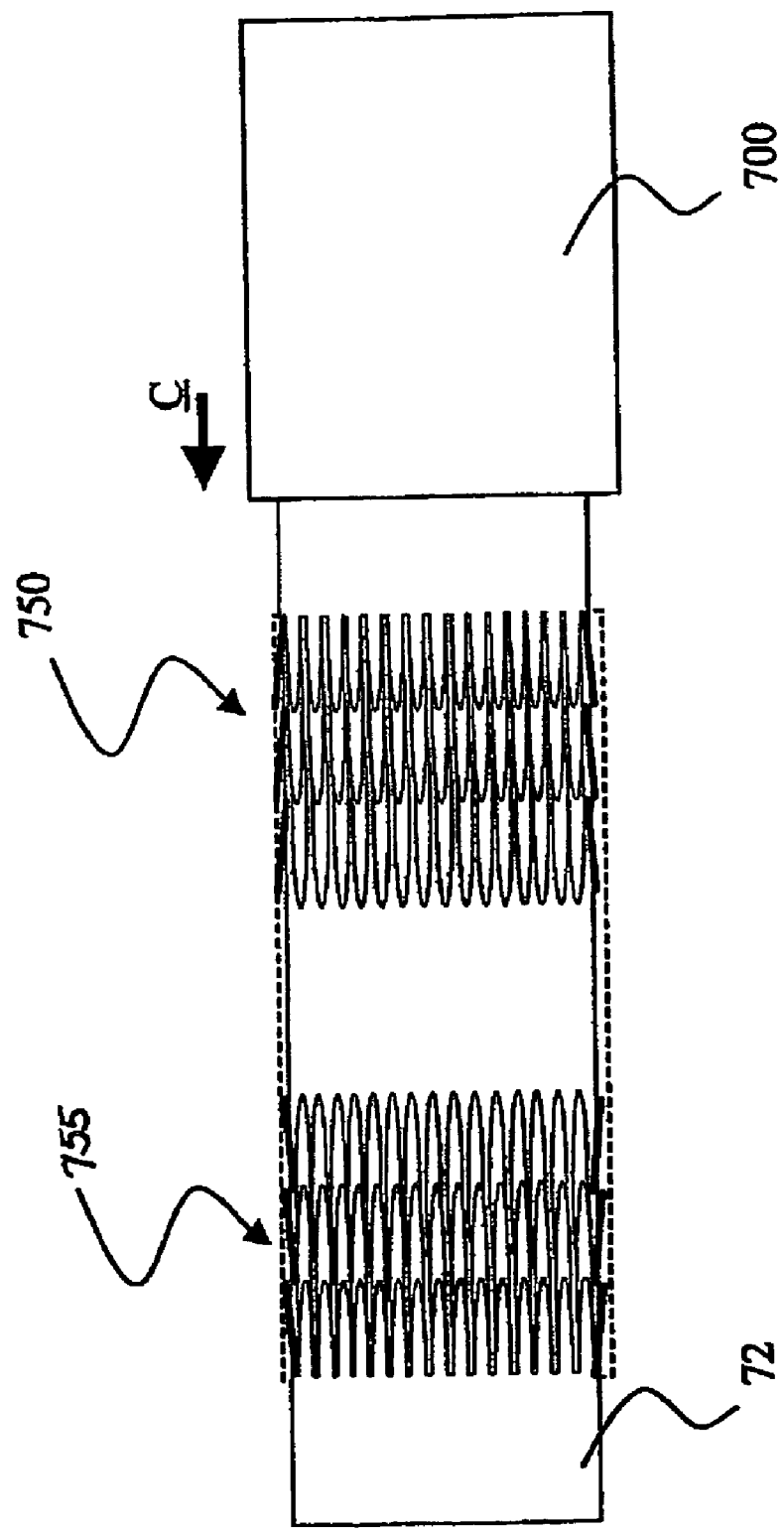

FIG. 7A-B are plan views of lead distal portions including retention means according to additional embodiments of the present invention, which incorporate dual retaining segments. FIG. 7A illustrates a lead body 71 including retaining segment 380, previously illustrated in FIG. 2A, and a second retaining segment 780 having projections extending in a generally opposite direction to those of segment 380; likewise FIG. 7B illustrates a lead body 72 including a retaining segment 750, including scale-like projections similar to that previously illustrated in FIG. 2D, and a second retaining segment 755 having projections extending in a generally opposite direction to those of segment 750. According to the illustrated embodiments, once lead bodies 71, 72 are positioned in a vessel for therapy delivery, the dual retaining segments prevent both further forward motion and rearward motion. FIGS. 7A-B further illustrate a tubular structure 700, which would be positioned over retaining segments 380 and 780 and 750 and 755, per arrow C, in order to shield the retaining segments during the positioning of lead bodies 71, 72; such a tubular structure may be a delivery or guiding catheter, examples of which are well known to those skilled in the art. According to an alternate embodiment a soluble coating, illustrated by dashed lines, as previously described in conjunction with FIG. 2B, temporarily covers retaining segments 380 and 780 and 750 and 755 during positioning of lead bodies 71, 72. It should be noted that further alternate embodiments of the present invention include any type of retaining segments having directional projections, similar to those illustrated in FIGS. 2A and 2D, formed as dual retaining segments as illustrated in FIGS. 7A-B.

Although embodiments of the present invention are described in the context of therapy delivery, diagnostic devices adapted for insertion within a blood vessel may also incorporate retention means described herein and thus fall within the scope of the present invention. In the foregoing detailed description, the invention has been described with reference to specific embodiments. However, it may be appreciated that various modifications and changes can be made without departing from the scope of the invention of the appended claims.

What is claimed is:

1. A medical lead, comprising:
   an elongate body having an electrical conductor therein;
   a first retaining segment, extending along a length of the body, forming a first fixed portion of an outer surface of the body and including a first end and a first plurality of projections extending in a first direction from the first portion of the outer surface, each of the first plurality of projections including a terminal edge directed toward the first end; and
   a second retaining segment, longitudinally separate and detached from the first retaining segment, extending along another length of the body, forming a second fixed portion of the outer surface of the body and including a second end opposite the first end, and a second plurality of projections extending in a second direction opposite the first direction from the second fixed portion of the outer surface, each of the second plurality of projections including a terminal edge directed toward the second end;
   wherein the first plurality of projections and the second plurality of projections are formed from a bioabsorbable material and are adapted to interfere with a wall of a vessel to retain the body within the vessel.

2. The medical lead of claim 1, wherein the first retaining segment is positioned proximal to the second retaining segment.

3. The medical lead of claim 1, wherein the first retaining segment and the second retaining segment each extend about an entire circumference of the body.

4. The medical lead of claim 1, wherein the first retaining segment and the second retaining segment each extend about a portion of a circumference of the body.

5. The medical lead of claim 1, wherein the body includes an elongate outer sheath and the first retaining segment and the second retaining segment are each an integral part of the sheath.

6. The medical lead of claim 1, wherein the first retaining segment and the second retaining segment are formed on a collar positioned about the body.

7. The medical lead of claim 1, further comprising a tubular structure deployable over the first plurality of projections and the second plurality of projections.

8. The medical lead of claim 1, wherein the body includes at least one pre-formed curve in proximity to the first retaining segment and the second retaining segment.

9. The medical lead of claim 1, wherein the first plurality of projections and the second plurality of projections are barb-like.

10. The medical lead of claim 1, wherein the first plurality of projections and the second plurality of projections are fish scale-like.

11. A medical lead, comprising:
    an elongate body having an electrical conductor therein;
    a first retaining segment, extending along a length of the body, forming a first fixed portion of an outer surface of the body and including a first end and a first plurality of projections extending from the first portion of the outer surface, each of the first plurality of projections including a terminal edge directed toward the first end; and
    a second retaining segment, longitudinally separate and detached from the first retaining segment, extending along another length of the body, forming a second fixed portion of an outer surface of the body and including a second end opposite the first end and a second plurality of projections extending from the second fixed portion of the outer surface, each of the second plurality of projections including a terminal edge directed toward the second end, wherein the first plurality of projections and the second plurality of projections are adapted to interfere with a wall of a vessel to retain the body within the vessel, the first retaining segment and the second retaining segment are formed on a collar positioned about the body, and the collar is formed from a bioabsorbable material.

12. A medical lead, comprising:
    an elongate body having an electrical conductor therein;
    a first retaining segment, extending along a length of the body, forming a first fixed portion of an outer surface of the body and including a first end and a first plurality of projections extending from the first portion of the outer surface, each of the first plurality of projections including a terminal edge directed toward the first end;
    a second retaining segment, longitudinally separate and detached from the first retaining segment, extending along another length of the body, forming a second fixed portion of an outer surface of the body and including a second end opposite the first end and a second plurality of projections extending from the second fixed portion of the outer surface, each of the second plurality of projections including a terminal edge directed toward the second end, wherein the first plurality of projections and the second plurality of projections are formed from a bioabsorbable material and are adapted to interfere with a wall of a vessel to retain the body within the vessel; and
    a dissolvable coating temporarily covering the first plurality of projections and the second plurality of projections.

13. A medical lead comprising
    an elongate body having an electrical conductor therein;

at least one retaining segment extending along a length of the body, the retaining segment including a first plurality of fish-like scales directed in a first common direction; and a second retaining segment, longitudinally separate and detached from the at least one retaining segment, extending along a length of the body, the second retaining segment including a second plurality of fish-like scales directed in a second common direction opposite to the first common direction;

wherein the first plurality of fish-like scales and the second plurality of fish-like scales are formed from a bioabsorbable material.

14. The medical lead of claim 13 wherein the first plurality of fish-like scales and the second plurality of fish-like scales are disposed in an overlapping pattern.

15. The medical lead of claim 13 wherein the first plurality of fish-like scales and the second plurality of fish-like scales are disposed in a plurality of circumferential rows and each individual one of the plurality of circumferential rows of scales is disposed in offset relation to an adjacent circumferential row of scales.

16. The medical lead of claim 13 wherein the elongated body has at least one preformed curved section in proximity to the retaining segment.

17. The medical lead of claim 16 wherein the curved section is disposed distally of the retaining segment.

18. The medical lead of claim 13 wherein the elongated body has a serpentine shape along the length thereof.

19. The medical lead of claim 13 wherein the elongate body is sized to move within a vessel and the retaining segment is characterized in allowing movement of the elongate body within the vessel in the common direction to an implanted position and preventing movement of the elongate body from the implanted position in an opposite direction to the common direction.

20. A medical lead comprising
an elongate body;
at least one retaining segment extending along a length of the body, the retaining segment including a first plurality of fish-like scales directed in a first common direction; and a second retaining segment, longitudinally separate and detached from the at least one retaining segment, extending along a length of the body, the second retaining segment including a second plurality of fish-like scales directed in a second common direction, wherein the elongate body includes a lead body having the retaining segment thereon, an electrode at one end of the lead body, a connector at an opposite end of the lead body from the electrode and a conductor electrically coupling the electrode to the connector;

wherein the first plurality of fish-like scales and the second plurality of fish-like scales are formed from a bioabsorbable material.

21. A medical lead comprising
an elongate body having an electrical conductor therein;
at least one retaining segment extending along a length of the body, the retaining segment including a first plurality of fish-like scales directed in a first common direction; and a second retaining segment, longitudinally separate and detached from the at least one retaining segment, extending along a length of the body, the second retaining segment including a second plurality of fish-like scales directed in a second common direction, wherein the elongated body has at least one preformed curved section in proximity to the retaining segment, and wherein the retaining segment is disposed in the curved section;

wherein the first plurality of fish-like scales and the second plurality of fish-like scales are formed from a bioabsorbable material.

22. A medical lead comprising
an elongate body having an electrical conductor therein;
at least one retaining segment extending along a length of the body, the retaining segment including a first plurality of fish-like scales directed in a first common direction;
a second retaining segment, longitudinally separate and detached from the at least one retaining segment, extending along a length of the body, the second retaining segment including a second plurality of fish-like scales directed in a second common direction; and
a dissolvable coating disposed over the retaining segment;
wherein the first plurality of fish-like scales and the second plurality of fish-like scales are formed from a bioabsorbable material.

23. A medical lead comprising:
an elongate body having an electrical conductor therein;
at least one retaining segment extending along a length of the body, the retaining segment including a first plurality of fish-like scales directed in a first common direction;
a second retaining segment, longitudinally separate and detached from the at least one retaining segment, extending along a length of the body, the second retaining segment including a second plurality of fish-like scales directed in a second common direction; and
a thin-walled tube disposed in concentric relation about the retaining segment;
wherein the first plurality of fish-like scales and the second plurality of fish-like scales are formed from a bioabsorbable material.

* * * * *